(12) United States Patent
Mehalebi et al.

(10) Patent No.: US 9,266,819 B2
(45) Date of Patent: Feb. 23, 2016

(54) WATER-SOLUBLE ANTIFOAM ADDITIVE FOR A CEMENT COMPOSITION, AQUEOUS SOLUTION CONTAINING SAME AND USE THEREOF IN MORTARS OR CONCRETES

(75) Inventors: Soraya Mehalebi, Poissy (FR); Anne-Elisabeth Desmotz, Carrieres sous Poissy (FR)

(73) Assignee: CIMENTS FRANCAIS, Puteaux (FR)

(*) Notice: Subject to any disclaimer, the term of this patent is extended or adjusted under 35 U.S.C. 154(b) by 0 days.

(21) Appl. No.: 13/994,270

(22) PCT Filed: Dec. 20, 2011

(86) PCT No.: PCT/FR2011/053099
§ 371 (c)(1),
(2), (4) Date: Jul. 22, 2013

(87) PCT Pub. No.: WO2012/085452
PCT Pub. Date: Jun. 28, 2012

(65) Prior Publication Data
US 2013/0291764 A1 Nov. 7, 2013

(30) Foreign Application Priority Data
Dec. 23, 2010 (FR) ...................................... 10 61184

(51) Int. Cl.
*C04B 24/12* (2006.01)
*C07C 229/12* (2006.01)
(Continued)

(52) U.S. Cl.
CPC ............. *C07C 229/12* (2013.01); *C04B 24/026* (2013.01); *C04B 40/0039* (2013.01); *C04B 2103/0067* (2013.01); *C04B 2103/50* (2013.01)

(58) Field of Classification Search
CPC ........................................................ C04B 24/12
USPC ................................ 106/696, 724, 727, 823
See application file for complete search history.

(56) References Cited

U.S. PATENT DOCUMENTS 4,285,733 A * 8/1981 Rosenberg et al. ........... 106/640
4,943,612 A * 7/1990 Morita et al. .................. 524/714
(Continued)

FOREIGN PATENT DOCUMENTS

EP 0 519 747 A2 12/1992
EP 0 752 465 A1 1/1997
(Continued)

OTHER PUBLICATIONS

Gritsai, L. I.; Yatsuk, L. V. Corporate Source: USSR Source: Stroitel'nye Materialy i Konstruktsii (1987), (1), 13 (abstract only).*
(Continued)

*Primary Examiner* — Paul Marcantoni
(74) *Attorney, Agent, or Firm* — Sofer & Haroun, LLP

(57) ABSTRACT

An anti-foam additive for a cement composition, including a fatty alcohol ester that is soluble in an aqueous medium at acidic pH, and hydrolysable in a basic medium, i.e. when the ester is incorporated into the cement composition, while releasing an active anti-foam molecule. This ester is preferably a fatty alcohol ester of a quaternary ammonium carboxylate, that is soluble in an aqueous solution of a superplasticizer, such as a polycarboxylate with poly(ethylene oxide) side chains. The additive can used for reducing the amount of air entrained during mixing or blending of mortars or concretes.

13 Claims, 1 Drawing Sheet

(51) Int. Cl.
*C04B 24/02* (2006.01)
*C04B 40/00* (2006.01)
C04B 103/00 (2006.01)
C04B 103/50 (2006.01)

(56) References Cited

U.S. PATENT DOCUMENTS

| | | | | |
|---|---|---|---|---|
| 5,709,739 | A * | 1/1998 | Wittich et al. | 106/38.22 |
| 7,662,225 | B2 * | 2/2010 | Antoine et al. | 106/277 |
| 7,772,300 | B2 * | 8/2010 | Schinabeck et al. | 524/44 |
| 8,097,666 | B2 * | 1/2012 | Macklin et al. | 524/4 |
| 8,158,699 | B2 * | 4/2012 | Freidrich et al. | 524/8 |
| 2005/0257720 | A1 | 11/2005 | Shendy et al. | |
| 2007/0163470 | A1 | 7/2007 | Chanut et al. | |
| 2007/0243321 | A1 | 10/2007 | Antoine et al. | |
| 2008/0280786 | A1 | 11/2008 | Reddy et al. | |
| 2011/0226164 | A1 * | 9/2011 | Andrioletti et al. | 106/810 |
| 2013/0130949 | A1 * | 5/2013 | Partain et al. | 507/216 |

FOREIGN PATENT DOCUMENTS

| | | |
|---|---|---|
| FR | 2 760 004 A1 | 1/1997 |
| FR | 2 866 330 A1 | 8/2005 |
| WO | 02/090285 A | 11/2002 |
| WO | 2005/121252 A1 | 12/2005 |

OTHER PUBLICATIONS

International Search Report, dated Jun. 11, 2012, from corresponding PCT application.

* cited by examiner

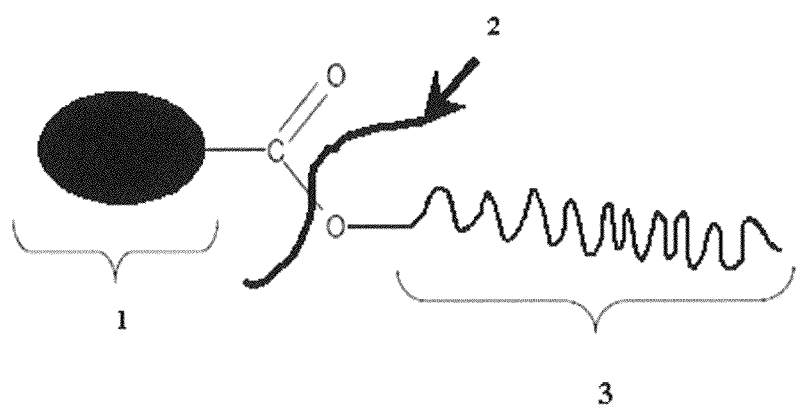

WATER-SOLUBLE ANTIFOAM ADDITIVE FOR A CEMENT COMPOSITION, AQUEOUS SOLUTION CONTAINING SAME AND USE THEREOF IN MORTARS OR CONCRETES

BACKGROUND OF THE INVENTION

1. Field of the Invention

The present invention relates to an anti-foam additive for a cementitious composition, to an aqueous solution incorporating said additive, and also to the use thereof in mortars or concretes.

2. Description of the Related Art

The formulation of high-performance concretes often requires plasticizers and superplasticizers either to increase the fluidity of the base cementitious composition at constant water input enabling the improvement of its workability, or for reducing the water content of the cementitious composition at equal consistency with a view to improving the mechanical strength and the durability.

is Among the plasticizers and superplasticizers, use is very often made of molecules chosen from polynaphthalene sulfonates, polymelamine sulfonates, lignosulfates (LS) and polycarboxylates, in particular polycarboxylates with polyethylene oxide side chains (PC-PEO) generally introduced in the form of an aqueous solution into the cementitious composition during the mixing and blending of concretes and mortars. The plasticizer and superplasticizer molecules have surface properties which give rise to air entrainment in the cementitious composition. This occluded air induces a modification of the rheology of the cementitious composition and a not inconsiderable drop in the mechanical strength both in the short term and in the long term of the mortar or concrete thus produced.

This phenomenon is observed more extensively with molecules of the LS and PC-PEO families.

In order to limit inclusion of air in the cementitious composition, anti-foams are generally introduced directly into the solutions of superplasticizers of LS or PC-PEO type so as to prevent the formation of air bubbles or to promote their destruction if they form.

Two constraints are linked to these anti-foam molecules. The first relates to the need to disperse the anti-foam in the aqueous solution of superplasticizer in order to sell a single product that provides the two functions (fluidification of the cementitious composition without excessive air entrainment), whilst the second constraint relates to the actual effectiveness of the anti-foam molecule with respect to the prevention or destruction of occluded air.

Anti-foam agents or defoaming agents are identical molecules, which only differ by their method of introduction into the medium. Specifically, anti-foam agents are introduced before the appearance of the foam in order to prevent the formation of stable gas/liquid interfaces, whilst defoaming agents are introduced after formation of the foam in order to eliminate it.

The present invention relates rather to the formation of anti-foam agents, that is to say additives intended to be introduced at the same time as the superplasticizer solution, into the cementitious composition, based on cement and water, at the time it is blended.

Anti-foam agents are, in general, hydrophobic formulations that are in the form of small-sized droplets that are insoluble beyond a limit in concentration in the liquid constituting the continuous phase, here the aqueous phase. The anti-foam agent is therefore by nature insoluble in the aqueous medium in which it forms an emulsion.

In order to be effective, the anti-foam agent must then migrate to the air/liquid film interface. During this migration, the anti-foam/liquid film and air/liquid film interfaces are replaced by an anti-foam/air interface. This transition requires a hydrophobic anti-foam agent since a hydrophilic formulation would remain within the aqueous phase.

The use of anti-foam agents for cementitious compositions such as cement grouts, mortars or concretes therefore requires dispersing the anti-foam agent in the aqueous superplasticizer solution. Since the anti-foam is by nature a hydrophobic molecule, insoluble in the aqueous medium, it is necessary to produce an emulsion of anti-foam in the aqueous superplasticizer solution.

In order to be marketable, this emulsion of anti-foam in the superplasticizer must be stable over the entire storage life (i.e. one year approximately) and over the range of temperatures to which the superplasticizers are commonly exposed (5-40° C. knowing that in general the emulsion is even less stable when the temperature is higher).

Furthermore, the anti-foam must also be effective in the cementitious medium over the entire processing time (i.e. from 15 minutes to several hours).

In addition, a loss of activity may be caused by a degradation of the anti-foam in the extremely basic medium of the cementitious compositions. The anti-foam molecules must be capable of withstanding this.

Moreover, "the depletion" of the anti-foam over time (resulting in a loss of effectiveness over time) is a well-known phenomenon which must not occur over the period of processing the cementitious compositions. This phenomenon often results from the reduction in size of the anti-foam droplets over time due to the shearing to which they are subjected.

In addition, the anti-foam must be able to be used with the conventional metering equipment. Certain anti-foam agents, such as tributyl phosphate, cause, for example, a degradation of certain pump bodies.

SUMMARY OF THE INVENTION

Consequently, a first objective of the invention is to provide an anti-foam agent that is stable in an aqueous solution, in particular in a superplasticizer solution, over the whole of the storage life before marketing, that is to say exhibiting no phase separation, for several months.

Another objective of the invention is to provide an anti-foam that is effective for preventing or limiting the incorporation of occluded air in cementitious compositions such as grouts, mortars or concretes, during the mixing and/or blending.

For this purpose, the present invention relates to an additive for a cementitious composition, based on cement and water, in particular for a cementitious composition prepared with addition of superplasticizer, characterized in that it is in the form of a fatty alcohol ester that is soluble in an aqueous medium at acid pH and hydrolysable during its incorporation into said cementitious composition, capable of releasing said fatty alcohol, the fatty alcohol being an active anti-foam molecule.

Since this fatty alcohol ester is hydrolysable during its incorporation into said cementitious composition, that is to say capable of releasing at least one active anti-foam molecule, it constitutes a precursor of said active anti-foam molecule.

The fact that the anti-foam additive is soluble in an aqueous medium at acid pH, preferably below 6, makes it possible to solve the problem of the stability of this additive in aqueous superplasticizer solutions, without phase separation. Thus there is also easy homogenization and therefore good distribution of the anti-foam in the whole of the superplasticizer solution.

Cementitious compositions, such as fresh cement grout, mortar or concrete, are highly basic media, for which the pH of the interstitial solution during mixing is very often greater than 12. At this pH value, the hydrolysis of the in situ anti-foam precursor therefore makes it possible to release the active molecule within the cementitious composition, where its presence is required for limiting or preventing the formation of air bubbles, in particular during the mixing with water and cement and the blending.

Preferably, the fatty alcohol ester is a fatty alcohol ester of a quaternary ammonium carboxylate, of general formula (I) below:

$$A^-, R_1R_2R_3N^+CH_2C(O)OR_4 \quad (I)$$

wherein the radicals $R_1$, $R_2$ and $R_3$, which are identical or different, are radicals chosen from hydrogen, substituted or unsubstituted, linear or branched $C_1$ to $C_{12}$ alkyl radicals, and $R_4$ is a saturated or unsaturated, substituted or unsubstituted, linear or branched $C_{10}$ to $C_{22}$ fatty alcohol hydrocarbon-based chain, A is a sulfonate anion, such as alkyl sulfonate, preferably a methyl sulfonate $CH_3SO_3^-$.

The ammonium carboxylate constitutes a hydrophilic part of the ester molecule which is soluble in an aqueous solution, whereas the fatty alcohol hydrocarbon-based chain is hydrophobic.

Preferably, the fatty alcohol ester is a fatty alcohol ester of an N,N,N-trialkyl glycine, with identical or different $C_1$ to $C_3$ alkyl radicals, preferably a fatty alcohol ester of N,N,N-trimethyl glycine, also referred to as fatty alcohol ester of glycine betaine.

Contrary to the prior art, more particularly the chapter "Anti-mousses et agents demoussants" ["Anti-foams and defoaming agents"] from Techniques de l'Ingénieur—J2—205, page 3, in which Vance BERGERON indicates that alcohols with a short hydrocarbon-based chain (less than 10 carbon atoms), may be added to aqueous solutions in order to destabilize a foam, and that, on the other hand, alcohols with a longer chain have an opposite effect and promote the stability of foams, the inventors have surprisingly observed that the fatty alcohols, capable of being released during the hydrolysis of the fatty alcohol ester in a basic medium, belonging to primary or secondary $C_{10}$ to $C_{22}$, preferably $C_{10}$ to $C_{18}$, alcohols which are saturated or comprise at least one double bond are particularly effective as an anti-foam.

Preferred fatty alcohols are chosen from decanol, undecanol, lauryl alcohol, tetradecanol, oleyl alcohol, 10-undecen-1-ol and 2-decanol. An additional advantage is that these released fatty alcohols are molecules that are natural and/or not very toxic for the environment, just like N,N,N-trialkyl glycine, extracted from beetroot.

The process for using the anti-foam additive, according to the invention, consists in introducing the fatty alcohol ester alone into the cementitious composition in the form of an aqueous solution of acid pH, preferably having a pH of less than 6, or advantageously into an aqueous solution of superplasticizer or of another adjuvant. According to one variant, it is not excluded to introduce this additive also in powder form into the cementitious composition, for example in the water intended for the mixing of the cementitious composition.

The present invention also relates to an aqueous solution of superplasticizer for a cementitious composition, characterized in that said aqueous solution comprises at least one superplasticizer, preferably a superplasticizer chosen from polycarboxylates with polyethylene oxide side chains, preferably poly(meth)acrylates with polyethylene oxide side chains, and at least one anti-foam additive in the form of a fatty alcohol ester, the superplasticizer and the anti-foam additive being dissolved in said aqueous solution.

Thus, a homogeneous solution containing both a superplasticizer and an anti-foam additive can be marketed and used easily either from the mixing onwards (introduced for example with the mixing water), or during the blending of the cementitious composition, made in the form of grout, mortar or concrete.

Advantageously, the anti-foam additive is present in the aqueous superplasticizer solution at a concentration between 0.01% and 5% by weight, preferably between 0.1% and 2% by weight, more preferably between 0.1% and 0.6% by weight, relative to the superplasticizer.

Finally, the anti-foam additive described above alone, in the form of powder or an aqueous solution, advantageously in solution in an aqueous superplasticizer solution as described above, finds an advantageous use in mortars or concretes for reducing the amount of air entrained during the mixing and blending of the cementitious composition, and more particularly for limiting the amount of occluded air in a fresh mortar to a value of less than 6% by volume, preferably less than 4.5% by volume (measured according to the standard NF EN 1015-7 method A) or in a fresh concrete to a value of less than 3% by volume.

The use of this anti-foam precursor is thus suitable for numerous cases where the cementitious composition contains adjuvants that may entrain air during the blending thereof.

The present invention also relates to a process for limiting the inclusion of air in a fresh mortar to a value of less than 6% by volume, preferably less than 4.5% by volume (value measured according to the standard NF EN 1015-7 method A) or in a fresh concrete to a value of less than 3% by volume, characterized in that it comprises the incorporation into the cementitious composition of the mortar or of the concrete during blending, in the mixing water or after addition of the mixing water, of a fatty alcohol ester as described above, preferably in the form of an aqueous solution at pH<6, that is hydrolysable during its incorporation into said cementitious composition and capable of releasing said fatty alcohol, the fatty alcohol being an active anti-foam molecule.

This process for limiting the inclusion of air may, as a variant, comprise the incorporation into the cementitious composition of the mortar or of the concrete during blending, in the mixing water or after addition of the mixing water, of an aqueous solution as described above, containing a superplasticizer and the anti-foam additive in the form of a fatty alcohol ester.

Since the concentration of superplasticizer can vary from 0.05% to 5%, preferably from 0.1% to 2% in the cementitious composition, the content of fatty alcohol ester according to the present invention is advantageously between 0.01% and 5% by weight, preferably between 0.1% and 2% by weight, more preferably between 0.1% and 0.6% by weight, relative to the superplasticizer.

The present invention will be illustrated by non-limiting examples described below, with reference to FIG. 1 which represents an anti-foam additive according to the present invention.

The materials and molecules used in the examples according to the invention and the comparative examples, and also the methods for evaluating their performances are the following:

1—Materials Used

Superplasticizer Solution

The superplasticizer used is an anionic polymer of polycarboxylate (PC) type substituted by polyethylene oxide (PEO) chain linkages, the chemical formula (II) of which is the following:

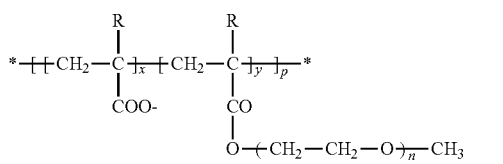

In the examples below, R is $CH_3$, it is therefore a polymethacrylate, with a degree of PEO grafting (y) of 28%, n the chain length of the PEOs being 15, x=72% since x+y=100 and p being between 10 and 100, and here close to 50. This polymer is put into solution in water at a concentration equal to 30% by weight. The pH of this solution is between 5 and 6.

Due to the proximity of the positive charge on the nitrogen and negative charge of the carboxylate function, the glycine betaine is very stable in an acid medium, in particular at the pH of the superplasticizer solution. In order to reinforce the stability and guarantee a stability over a long period, it is possible to further acidify the superplasticizer solution.

Various molecules bearing hydrophobic chains, such as various fatty alcohols with various chain lengths, have been grafted to the carboxylate function. These esters have been prepared according to the method described in patent EP 1 742 999 B1. These esters of the glycine betaine are stable at acid pH and are hydrolyzed at pH values above 6.5, releasing the corresponding alcohol (see, for example, the stability study of octadecyl betaine mesylate in this patent).

At the pH of the cementitious compositions (pH>12), the hydrolysis is virtually complete and instantaneous. The fatty alcohol and the glycine betaine are then released.

Reaction IV below illustrates the hydrolysis of an ester of glycine betaine with oleyl alcohol:

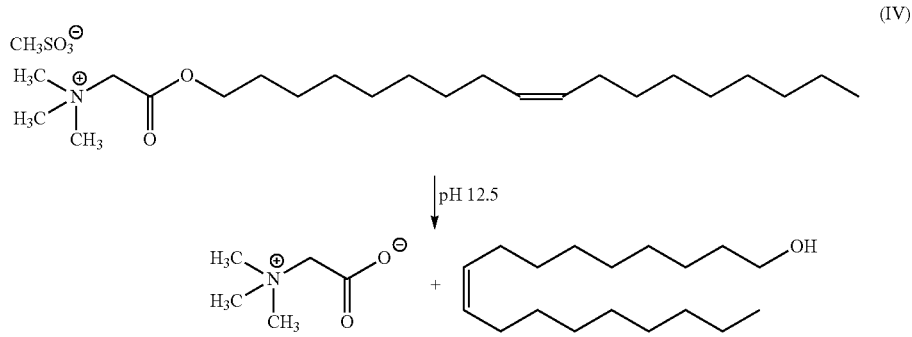

Anti-foam Additive

BRIEF DESCRIPTION OF THE DRAWING FIGURES

A diagram illustrating an anti-foam additive molecule in accordance with the present invention is represented in FIG. 1.

DETAILED DESCRIPTION OF THE INVENTION

The anti-foam additive is a molecule comprising both a polar head 1 and a hydrophobic chain 3, the two being linked by a carboxylate function, one of the bonds of which is, according to the arrow 2, hydrolysable at basic pH, that is to say at the pH of the cement formulations close to 12.5, making it possible to release the hydrophobic chain.

A diagram illustrating this molecule is represented in FIG. 1.

In the examples presented, the polar head is the glycine betaine of formula (III) below, which is a quaternary trimethylalkylammonium with a carboxylate function.

The fatty alcohols tested are both saturated or unsaturated primary alcohols and a secondary alcohol.

The additive according to the invention, in the form of a precursor ester of the active anti-foam molecule, was dissolved in the aqueous superplasticizer solution. The ester percentages are expressed as a percentage by weight relative to the weight of the superplasticizer in said aqueous solution.

A fraction of this aqueous solution containing the superplasticizer and the anti-foam precursor was added to a cementitious composition in the form of a concrete-equivalent mortar (CEM: see next paragraph) during the blending.

Concrete-Equivalent Mortar (CEM)

The cementitious composition on which the various aqueous solutions of a mixture of superplasticizer with various amounts of additive were tested were tested on a concrete-equivalent mortar (CEM* developed by CTG). This mortar composition is the following:
- 680 g of cement (CEM I 52.5)
- 1350 g of CEM* sand
- 303 g of water,
- 2 g of PC-PEO superplasticizer, i.e. 0.3% of the mass of cement.

(* La méthode du mortier de béton equivalent (MBE). Un nouvel outil d'aide à la formulation des bétons adpvantés [The concrete-equivalent mortar (CEM) method. A new tool for assisting in the formulation of admixture-containing concretes]. A. Schwatzentruber, C. Catherine, Materials and Structures, Vol. 33, October 2000, pp. 475-482)

The detailed procedure for preparing the concrete-equivalent mortar is described in the above document, the superplasticizer here being added after the mixing water (that is to say "at a later stage") at the end of blending.

2—Evaluation Methods

The fresh mortar spreading measurement was carried out according to the method described in the article above (concrete-equivalent mortar method).

All the tests carried out were implemented so that the reference spreading in millimeters is always close to 210 mm with the superplasticizer without addition of the anti-foam additive.

Consequently, the concentration of superplasticizer with respect to the cement always remained identical (0.3% by weight relative to the cement) in all of the tests (comparative examples—examples according to the invention) presented below.

For the evaluation of the effectiveness of the anti-foam, the standard NF EN 1015-7 method A was used. The measurements of the amount of occluded air in the mortar were carried out on the fresh mortar (CEM*) at the end of the blending.

COMPARATIVE EXAMPLES

Tested separately in these examples were the molecules of glycine betaine and oleyl alcohol ($C_{18}$ fatty alcohol), alone or in combination, dissolved in an aqueous solution containing 30% by weight of the superplasticizer described in point 1-above. The results of the tests carried out on the CEM mortar are assembled in Table 1.

TABLE 1

| Formulation | 0 | 1 | 2 | 3 | 4 | 5 | 6 |
| --- | --- | --- | --- | --- | --- | --- | --- |
| % oleyl alcohol | / | 0.20 | / | 0.20 | 0.40 | / | 0.40 |
| % glycine betaine | / | / | 0.09 | 0.09 | / | 0.175 | 0.175 |
| Results | | | | | | | |
| Spreading (mm) | 199 | 222 | 218 | 223 | 229 | 213 | 235 |
| Occluded air (% by volume) | 10 | 6.2 | 9.8 | 4.2 | 2.6 | 12 | 2.4 |

The percentages of oleyl alcohol and of glycine betaine are expressed by weight relative to the superplasticizer.

The accuracy of the spreading measurement is plus or minus 10 mm, for the occluded air this accuracy is plus or minus 2% (for air values greater than 7%) and the uncertainty becomes plus or minus 0.5% for low values.

From these tests, it is observed that the addition of oleyl alcohol significantly reduces the entrained air, the value changing from 10% to around 6% at 0.2% oleyl alcohol and falling to a value close to 2% with 0.4% oleyl alcohol.

The effect of the glycine betaine alone is negligible, but appears to be fairly positive in synergy with oleyl alcohol.

EXAMPLES ACCORDING TO THE INVENTION

In these examples, the fatty alcohol was not added directly to the superplasticizer solution, but dissolved in the form of its precursor, the fatty alcohol glycine betaine ester.

Various esters tested and also the values observed for various amounts of esters with respect to the superplasticizer are assembled in Table 2.

The content of superplasticizer was 0.3% by weight/cement. The amount of ester is expressed in % by weight relative to the superplasticizer (value of the solids content of the aqueous solution).

TABLE 2

| Compounds (according to the invention) | Spreading (mm) | Entrained air (%) |
| --- | --- | --- |
| Superplasticizer alone | 214 | 12 |
| + unsaturated $C_{18}$ (oleyl) glycine betaine ester | | |
| 0.10% | 208 | 11.5 |
| 0.20% | 209 | 12.5 |
| 0.41% | 212 | 12 |
| 1.14% | 206 | 11.5 |
| 2.09% | 211 | 8.5 |
| + $C_{12}$ (lauryl) glycine betaine ester | | |
| 0.59% | 218 | 5.6 |
| 2.00% | 220 | 3.2 |
| + $C_{10}$ (decanol) glycine betaine ester | | |
| 0.62% | 225 | 7.2 |
| 2% | 214 | 3.2 |
| + $C_{14}$ (tetradecanol) glycine betaine ester | | |
| 0.40% | 206 | 7.6 |
| 2.00% | 218 | 4.2 |
| + $C_{11}$ (undecanol) glycine betaine ester | | |
| 0.44% | 211 | 6.4 |
| 2.00% | 209 | 3.2 |

TABLE 2-continued

| | Spreading (mm) | Entrained air (%) |
| --- | --- | --- |
| + unsaturated $C_{11}$ (10-undecan-1-ol) glycine betaine ester | | |
| 0.43% | 201 | 12.5 |
| 2.00% | 217 | 2.8 |
| + secondary $C_{10}$ (2-decanol) glycine betaine | | |
| 0.38 | 211 | 13 |
| 2.00 | 221 | 3 |
| Comparative example Superplasticizer + (oleyl) glycine betaine amide derivative | | |
| 1% | 202 | 15 |

In this Table 2, it is observed that the spreading is virtually unmodified irrespective of the nature of the ester and irrespective of its concentration. However, the entrained air values are variable but in most cases a value of less than 10% is observed.

The lowest values of less than 4.5% occluded air are obtained for concentrations close to 2% by weight of ester relative to the superplasticizer and for esters prepared with $C_{10}$ to $C_{14}$ fatty alcohols.

By way of comparison, an amide that can release a C18 (oleyl) amide was tested at 1% by weight relative to the superplasticizer in a superplasticizer solution. The amount of entrained air measured was 15%, i.e. a value much higher than the reference value of 12% with the superplasticizer alone. The amide therefore has an opposite effect (that is to say an increase of the entrained air) to that of the fatty alcohol ester of the present invention.

Furthermore, amides are stable up to a basic pH, only releasing fatty amines beyound a pH of around 8 or 9, whereas the fatty alcohols are released from the esters according to the invention starting from a pH of greater than or equal to 6.5, the hydrolysis of the precursor being complete at pH 9. The active agent according to the present invention is therefore available more rapidly in the cementitious composition, even before the formation of bubbles (foam).

It is therefore assumed that these fatty alcohol esters which have a high solubility in the aqueous superplasticizer solution are perfectly suitable for limiting, or even reducing, the content of entrained air in cementitious compositions.

It has been observed that the aqueous solutions of superplasticizer and of the anti-foam precursor according to the invention are perfectly stable at pH values ≤5.5 and exhibit no cloudiness or phase separation, for at least one year.

The invention claimed is:

1. An aqueous solution of superplasticizer for a cementitious composition, comprising:
at least one superplasticizer selected from the groupconsisting of polycarboxylates with polyethylene oxide side chains and poly(meth)acrylates with polyethylene oxide side chains, and at least one anti-foam additive in the form of a fatty alcohol ester that is soluble in an aqueous medium at acid pH and hydrolysable during incorporation into said cementitious composition, capable of releasing said fatty alcohol, the fatty alcohol being an active anti-foam molecule, the superplasticizer and the anti-foam additive being dissolved in said aqueous solution.

2. The aqueous solution as claimed in claim 1, wherein a concentration of anti-foam additive is between 0.01% and 5% by weight relative to the superplasticizer.

3. A process for limiting the inclusion of air in a mortar to a value of less than 6% by volume (value measured according to the standard NF EN 1015-7 method A) or in a concrete to a value of less than 3% by volume, the process comprising;
incorporating into the cementitious composition of the mortar or of the concrete during blending, in the mixing water or after addition of the mixing water, of a fatty alcohol ester as claimed in claim 1, that is hydrolysable during incorporation into said cementitious composition and capable of releasing said fatty alcohol, the fatty alcohol being an active anti-foam molecule.

4. A process for limiting the inclusion of air in a mortar to a value of less than 6% by volume (value measured according to the standard NF EN 1015-7 method A) or in a concrete to a value of less than 3% by volume, the process comprising:
incorporating into the cementitious composition of the mortar or of the concrete during blending, in the mixing water or after addition of the mixing water, of an aqueous solution as claimed in claim 1, containing a superplasticizer and the anti-foam additive in the form of a fatty alcohol ester.

5. A mortar or concrete, comprising:
cement;
water;
superplasticizer selected from the group consisting of lignosulfonates and polycarbonates with polyethylene oxide side chains; and
an anti-foam additive in the form of a fatty alcohol ester that is soluble in an aqueous medium at acidic pH and hydrolysable during incorporation into said cement that releases said fatty alcohol, the fatty alcohol being an active anti-foam molecule, the fatty alcohol ester being a fatty alcohol ester of a quaternary ammonium carboxylate, of general formula (I) below:

$$A^-, R_1R_2R_3N^+CH_2C(0)OR_4 \qquad (I)$$

where the radicals $R_1$, $R_2$ and $R_3$, which are identical or different, are radicals selected from the group consisting of hydrogen, substituted or unsubstituted, linear or branched $C_1$ to $C_{12}$ alkyl radicals, and $R_4$ is a saturated or unsaturated, substituted or unsubstituted, linear or branched $C_{10}$ to $C_{22}$ fatty alcohol hydrocarbon chain, A is a sulfonate anion,
the anti-foam additive being present in an amount effective to reduce an amount of air entrained during mixing and blending of the mortar or concrete.

6. The mortar or concrete as claimed in claim 5, wherein the amount of occluded air in a mortar is less than 6% by volume, or in a concrete is less than 3% by volume, as measured according to standard NF EN 1015-7 method A.

7. The mortar or concrete as claimed in claim 5, wherein the sulfonate ion is an alkyl sulfonate.

8. The mortar or concrete as claimed in claim 5, wherein the sulfonate ion is methyl sulfonate.

9. The mortar or concrete as claimed in claim 5, wherein the fatty alcohol ester is a fatty alcohol ester of an N,N,N-trialkyl glycine, with identical or different $C_1$ to $C_3$ alkyl radicals.

10. The mortar or concrete as claimed in claim 5, wherein the fatty alcohol (capable of being released during the hydrolysis of the ester in a basic medium) is a primary or secondary $C_{10}$ to $C_{22}$ alcohol that is saturated or that comprises at least one double bond.

11. The mortar or concrete as claimed in claim 5, wherein the fatty alcohol is selected from the group consisting of decanol, undecanol, lauryl alcohol, tetradecanol, oleyl alcohol, 10-undecen-1-ol and 2-decanol.

12. The mortar or concrete as claimed in claim 5, wherein the fatty alcohol ester is a fatty alcohol ester of N,N,N-trimethyl glycine.

13. The mortar or concrete as claimed in claim 5, wherein the pH is less than 6.

\* \* \* \* \*